(12) United States Patent
Acker et al.

(10) Patent No.: US 6,253,770 B1
(45) Date of Patent: Jul. 3, 2001

(54) CATHETER WITH LUMEN

(75) Inventors: David E. Acker, Setauket, NY (US);
Marcus J. Millet, Westfield, NJ (US);
Maier Fenster, Petach Tikva (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/117,782

(22) PCT Filed: Feb. 14, 1997

(86) PCT No.: PCT/US97/02617

§ 371 Date: Jan. 11, 1999

§ 102(e) Date: Jan. 11, 1999

(87) PCT Pub. No.: WO97/29684

PCT Pub. Date: Aug. 21, 1997

Related U.S. Application Data

(60) Provisional application No. 60/012,242, filed on Feb. 26, 1996.

(30) Foreign Application Priority Data

Feb. 15, 1996 (IT) .......................................... 117148
Sep. 17, 1996 (IT) .......................................... 119262

(51) Int. Cl.⁷ .................................................. A61B 5/05
(52) U.S. Cl. .......................................................... 128/899
(58) Field of Search ............. 600/28, 424; 128/897–899

(56) References Cited

U.S. PATENT DOCUMENTS

| 3,644,825 | 2/1972 | Davis, Jr. et al. . |
|---|---|---|
| 3,868,565 | 2/1975 | Kuipers . |
| 4,017,858 | 4/1977 | Kuipers . |
| 4,054,881 | 10/1977 | Raab . |
| 4,560,930 | 12/1985 | Kouno . |
| 4,570,354 | 2/1986 | Hindes . |
| 4,592,356 | 6/1986 | Gutierrez . |
| 4,613,866 | 9/1986 | Blood . |
| 4,642,786 | 2/1987 | Hansen . |
| 4,651,436 | 3/1987 | Gaal . |
| 4,710,708 | 12/1987 | Rorden et al. . |
| 4,788,987 | 12/1988 | Nickel . |
| 4,813,935 | 3/1989 | Haber et al. ............................ 604/99 |

(List continued on next page.)

FOREIGN PATENT DOCUMENTS

| WO 94/00050 | 1/1994 | (WO) . |
|---|---|---|
| WO 94/04938 | 3/1994 | (WO) . |
| WO 94/06349 | 3/1994 | (WO) . |
| WO 94/23647 | 10/1994 | (WO) . |
| WO 94/28782 | 12/1994 | (WO) . |
| WO 95/05773 | 3/1995 | (WO) . |
| WO 95/07657 | 3/1995 | (WO) . |
| WO 95/09562 | 4/1995 | (WO) . |
| WO 95/10226 | 4/1995 | (WO) . |
| WO 95/19738 | 7/1995 | (WO) . |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al. "Transmyocardial Laser Revascularization: A Review" Journal of Clinical Laser Medicine & Surgery. vol. 11(1993) pp. 15–19. \

*Primary Examiner*—Samuel G. Gilbert
(74) *Attorney, Agent, or Firm*—Louis J. Capezzuto

(57) ABSTRACT

The invention is a catheter (20) with a lumen (24) wherein the lumen is obstructed by a portion of the catheter (50). The catheter (20) includes a position detector (22) at the tip of the catheter (20).

19 Claims, 14 Drawing Sheets

U.S. PATENT DOCUMENTS

| | | |
|---|---|---|
| 4,849,692 | 7/1989 | Blood . |
| 4,869,238 | 9/1989 | Opie et al. . |
| 4,905,698 | 3/1990 | Strohl, Jr. et al. . |
| 4,917,095 | 4/1990 | Fry et al. . |
| 4,921,482 | 5/1990 | Hammerslag et al. . |
| 4,931,059 | 6/1990 | Markham . |
| 4,945,305 | 7/1990 | Blood . |
| 5,002,137 | 3/1991 | Dickinson et al. . |
| 5,042,486 | 8/1991 | Pfeiler et al. . |
| 5,059,197 | 10/1991 | Urie et al. . |
| 5,078,144 | 1/1992 | Sekino et al. . |
| 5,099,845 | 3/1992 | Besz et al. . |
| 5,125,924 | 6/1992 | Rudko . |
| 5,125,926 | 6/1992 | Rudko et al. . |
| 5,158,084 | 10/1992 | Ghiatas . |
| 5,172,056 | 12/1992 | Voision . |
| 5,195,540 | 3/1993 | Shiber . |
| 5,195,968 | 3/1993 | Lundquist et al. . |
| 5,197,482 | 3/1993 | Rank et al. . |
| 5,211,165 | 5/1993 | Dumoulin et al. . |
| 5,215,680 | 6/1993 | D'Arrigo . |
| 5,217,484 | 6/1993 | Marks . |
| 5,234,426 | 8/1993 | Rank et al. . |
| 5,251,635 | 10/1993 | Dumoulin et al. . |
| 5,253,647 | 10/1993 | Takahashi et al. . |
| 5,255,680 | 10/1993 | Darrow et al. . |
| 5,265,610 | 11/1993 | Darrow et al. . |
| 5,267,960 | 12/1993 | Hayman et al. . |
| 5,273,025 | 12/1993 | Sakiyama et al. . |
| 5,275,166 | 1/1994 | Vaitekunas et al. . |
| 5,295,484 | 3/1994 | Marcus et al. . |
| 5,295,486 | 3/1994 | Wollschager et al. . |
| 5,301,682 | 4/1994 | Debbas . |
| 5,309,913 | 5/1994 | Kormos et al. . |
| 5,325,873 | 7/1994 | Hirschi et al. . |
| 5,368,564 | 11/1994 | Savage . |
| 5,368,592 | 11/1994 | Stern et al. . |
| 5,373,849 | 12/1994 | Maroney et al. . |
| 5,375,596 | 12/1994 | Twiss et al. . |
| 5,377,678 | 1/1995 | Dumoulin et al. . |
| 5,380,316 | 1/1995 | Aita et al. . |
| 5,383,454 | 1/1995 | Bucholz . |
| 5,383,874 | 1/1995 | Jackson et al. . |
| 5,383,923 | 1/1995 | Webster, Jr. . |
| 5,385,148 | 1/1995 | Lesh et al. . |
| 5,389,096 | 2/1995 | Aita et al. . |
| 5,391,199 | 2/1995 | Ben Haim . |
| 5,403,356 | 4/1995 | Hill et al. . |
| 5,404,297 | 4/1995 | Birk et al. . |
| 5,409,004 | 4/1995 | Sloan . |
| 5,423,321 | 6/1995 | Fontenot . |
| 5,425,367 | 6/1995 | Shapiro et al. . |
| 5,425,382 | 6/1995 | Golden et al. . |
| 5,429,132 | 7/1995 | Guy et al. . |
| 5,431,168 | 7/1995 | Webster, Jr. . |
| 5,433,198 | 7/1995 | Desai . |
| 5,437,277 | 8/1995 | Dumoulin et al. . |
| 5,437,659 * | 8/1995 | Leckrone ................................ 606/7 |
| 5,443,489 | 8/1995 | Ben-Haim . |
| 5,450,846 | 9/1995 | Goldreyer . |
| 5,465,717 | 11/1995 | Imran et al. . |
| 5,471,982 | 12/1995 | Edwards et al. . |
| 5,471,988 | 12/1995 | Fujio et al. . |
| 5,480,422 | 1/1996 | Ben-Haim . |
| 5,483,951 | 1/1996 | Frassica et al. . |
| 5,487,391 | 1/1996 | Panescu . |
| 5,538,008 | 7/1996 | Crowe . |
| 5,554,152 | 9/1996 | Aita et al. . |
| 5,555,883 | 9/1996 | Avitall . |
| 5,558,091 | 9/1996 | Acker et al. . |
| 5,558,092 | 9/1996 | Unger et al. . |
| 5,577,502 | 11/1996 | Darrow et al. . |
| 5,588,432 | 12/1996 | Crowley . |
| 5,617,857 | 4/1997 | Chader et al. . |
| 5,622,169 | 4/1997 | Golden et al. . |
| 5,715,822 | 2/1998 | Watkins et al. . |
| 5,729,129 | 3/1998 | Acker . |
| 5,795,325 * | 8/1998 | Valley et al. ............................ 604/53 |
| 5,833,650 * | 11/1998 | Imran ..................................... 604/53 |
| 5,906,575 * | 5/1999 | Conway et al. ......................... 600/29 |
| 6,048,333 * | 4/2000 | Lennox et al. ......................... 604/113 |

FOREIGN PATENT DOCUMENTS

| | | |
|---|---|---|
| WO 96/05768 | 2/1996 | (WO) . |
| WO 96/41119 | 12/1996 | (WO) . |
| WO 97/03609 | 2/1997 | (WO) . |
| WO 97/29678 | 8/1997 | (WO) . |
| WO 97/29679 | 8/1997 | (WO) . |
| WO 97/29683 | 8/1997 | (WO) . |
| WO 97/29684 | 8/1997 | (WO) . |
| WO 97/29685 | 8/1997 | (WO) . |
| WO 97/29701 | 8/1997 | (WO) . |
| WO 97/29709 | 8/1997 | (WO) . |
| WO 97/29710 | 8/1997 | (WO) . |
| WO 97/29803 | 8/1997 | (WO) . |
| WO 97/32179 | 9/1997 | (WO) . |

* cited by examiner

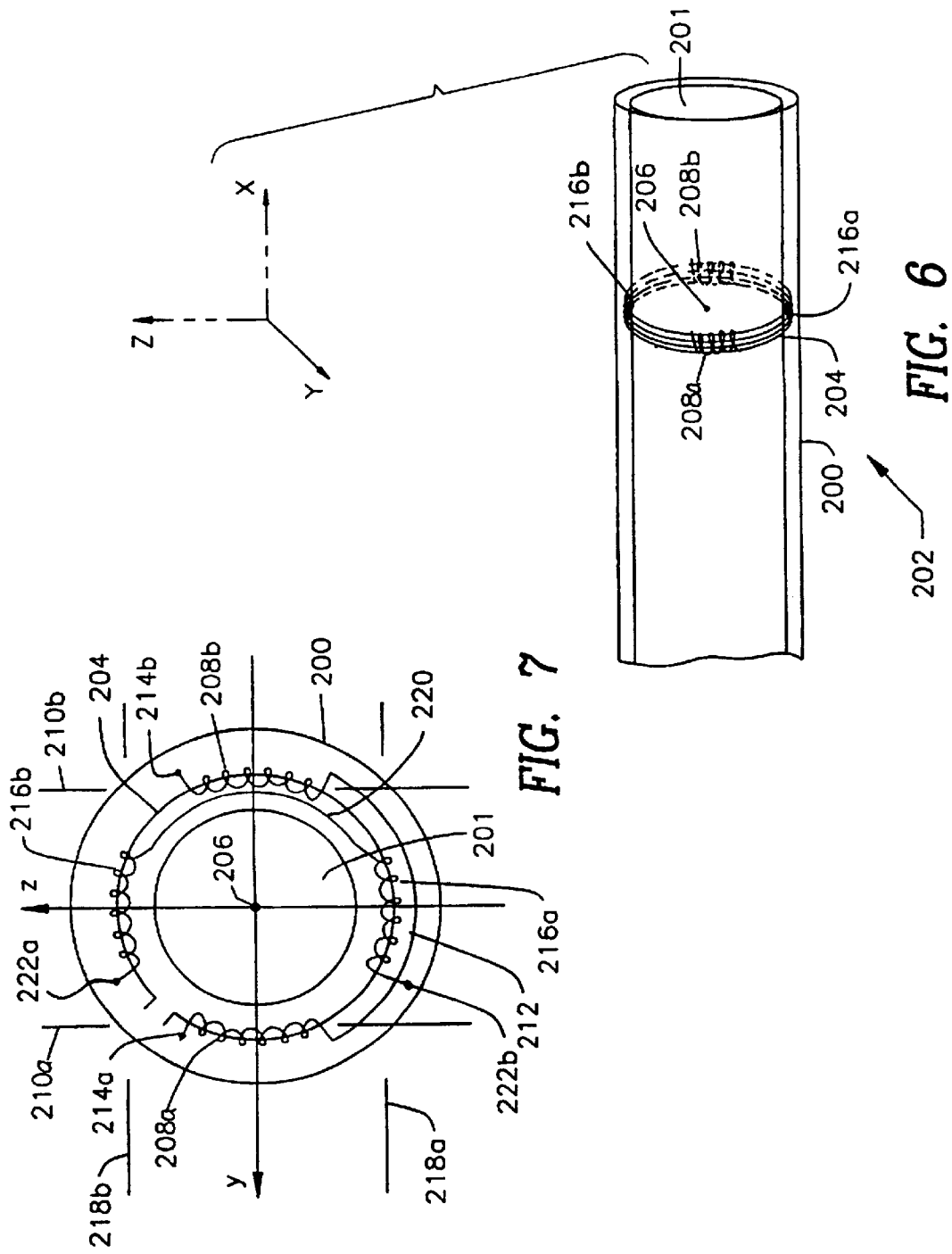

CATHETER WITH LUMEN

This application claims benefit of provisional application 60/012,242 filed Feb. 26, 1996.

TECHNICAL FIELD

The present invention relates to medical instruments, and more specifically relates to medical instruments such as catheters having internal lumens and having sensors for detecting the position or orientation of the instrument.

BACKGROUND ART

Many minimally invasive medical procedures are performed using a catheter with a lumen. For example, in angioplasty, a balloon is inflated using saline solution conveyed through a lumen. In many cases it is desirable to inject medicine or radio-opaque dyes through a catheter's lumen. In some procedures, a tool is guided through the lumen. After the use of the tool is completed, the tool is retracted and may be replaced by another tool.

U.S. Pat. Nos. 5,480,422, 5,383,454, 5,295,486 and 5,437,277 and PCT application PCT/US95/01103, the disclosures of which are incorporated herein by reference, describe a few of the many types of position sensing tips for catheters. The position sensor in the catheter tip allows the physician to monitor location of the tip within the body without continually imaging the body and catheter. This capability can significantly reduce the radiation exposure of the patient and of the physician. For many position sensors size is an important factor. In some cases, the larger the sensor the more precise the position estimate. The maximum size of the position sensor typically is limited by the diameter of the catheter. In general, catheters with a smaller diameter are more flexible and can be used in a larger portion of the vascular system than catheters with a large diameter.

It is difficult to accommodate both a large lumen and a position sensor in the tip of a catheter, since the position sensor typically occupies almost the entire cross-section of the catheter.

DISCLOSURE OF THE INVENTION

It is an object of one aspect of the present invention to provide a catheter or other similar medical probe having both a position sensor at its tip and a large lumen.

A catheter according to one aspect of the invention includes a body defining a lumen and further includes a sensor such as a position sensor mounted to the body at a sensor location. Typically, the body and lumen are elongated, and the sensor location is adjacent the distal tip of the body. The catheter is adjustable between two configurations. In a first configuration, the lumen is constricted and/or obstructed by the sensor and the catheter has a first diameter at the sensor location. The first diameter at the sensor location may be similar to the diameter of the rest of the catheter. In a second configuration, the catheter is expanded at the sensor location so that the catheter has a second diameter at the sensor location, larger than the first diameter. In the second configuration, the constriction or obstruction of the lumen by the sensor is reduced or eliminated. Typically, the second diameter of the catheter at the sensor location is larger than the diameter of the rest of the catheter. As used herein with reference to an elongated body such as a catheter, the term "diameter" means the maximum dimension of the object transverse to the direction of elongation. The catheter body may be expanded at the sensor location by inflating a balloon in the body. Alternatively or additionally, a stylet is either inserted or removed from the lumen to affect a change in the shape of the lumen.

In another preferred embodiment of the present invention, a catheter including a body with a lumen and a position sensor has two configurations. In a first configuration, the lumen runs the entire length of the catheter but is obstructed by the position sensor at the tip of the catheter. In a second configuration, the distal end of tip of the catheter is moved aside so that it does not block the lumen. Preferably, the distal tip is shunted aside at a known orientation relative to the long axis of the catheter. Alternatively, the distal end of the tip of the catheter, which contains the position sensor is folded back onto the catheter. Preferably, the distal end of the tip is secured in a known position after such movement, for example, securing it in a socket.

Preferably, the catheter changes between configurations by inserting or by removing a stylet from the lumen. Alternatively, the change is achieved using a piezoelectric actuator.

In a preferred embodiment of the invention, the catheter is constrained in an obstructed configuration by a rigid sheath. When the sheath is moved from the catheter tip, the catheter changes configuration to the non-obstructed configuration. The catheter may change configuration due to its own resilience. That is, the catheter is resiliently biased to the non-obstructed configuration.

Another embodiment of the invention relates to a catheter having an elongated body defining an axis and an axially-extensive lumen. The catheter further includes a position sensor. The position sensor comprises at least one lateral sensing coil having windings which are not coaxial with the catheter. Stated another way, the windings of the lateral sensing coil do not lie in planes perpendicular to the axis of the catheter body, so that the voltage induced on the coil has components representing changes in magnetic field in a lateral direction orthogonal to the axis of the catheter body. In one embodiment, the lateral sensing coil is formed as at least two portions, which are spaced apart from one another along the long axis of the catheter. Thus, the lateral sensing coil obstructs the passage of a lumen only half as much as a coil formed in a single portion. Alternatively or additionally, portions of the lateral sensing coil may be disposed on opposite sides of the lumen, and may be spaced apart from one another in a direction transverse to the axis.

In another embodiment, the windings of the lateral sensing coil may extend around the lumen. Thus, the windings of the lateral sensing coil may be disposed in planes oblique to the lengthwise axis of the lumen. The lateral sensing coil as a whole is coaxial with the catheter, but the windings are not perpendicular to the axis of the coil. Alternatively, the lateral sensing coil a may be a thin coil oriented at an angle of less than 90 degrees to the long axis of the catheter.

Yet another aspect of the invention provides a probe comprising a body defining a lumen and a plurality of transducer assemblies mounted to said body around said lumen. Each transducer assembly includes one or more transducers such as coils or other transducers. The different transducer assemblies are sensitive to field components such as magnetic or electromagnetic field components in different directions. Each transducer assembly has a center of sensitivity representing the sensitivity of the transducer or transducers in such assembly. As further discussed below, the center of sensitivity of a transducer assembly is the locus of the midpoint of the sensitivity of the entire transducer assembly, i.e., the locus of a theoretical point transducer having the same response as the transducer assembly. Preferably, the centers of sensitivity of all of the transducer assemblies are disposed at a common point. Stated another way, when exposed to a field, all of the transducers will act cooperatively as a multidirectional point sensor disposed at the common point. The common point may be located within the lumen of the probe. As further discussed below, this simplifies the mathematics required to deduce values such as position and orientation of the probe from the signals obtained by the transducers.

Preferably, a first transducer assembly includes a first coil such as a helical coil having turns encircling the lumen and having a coil axis extending in a first direction codirectional with said lumen. A second transducer assembly includes a pair of second coils disposed on opposite sides of the lumen. The second coils have axes extending in a second direction transverse to said first direction. Preferably, the second coils are aligned with one another in the first direction but are offset from one another in a third direction transverse to said first and second directions. As further explained below, the first assembly is sensitive to changes in the field component in the lengthwise direction along the lumen, and has a center of sensitivity at a common point on the central axis of the lumen. The second assembly is sensitive to changes in the field component in a second, lateral direction transverse to the lengthwise direction and desirably orthogonal to the lengthwise direction. The center of sensitivity of the second or lateral direction transducer assembly is disposed at the same common point on the central axis of the lumen.

The probe may further include a third transducer assembly including a pair of third coils disposed on opposite sides of said lumen, the axes of said third coils extending in said third direction, the axes of said third coils being offset from one another in said second direction.

In one preferred arrangement, the turns of the second and third coils encircle the turns of the first coil. In another arrangement, the first coil includes a pair of sections spaced apart from one another in the first or lengthwise direction. The second and third coils are disposed between the sections of the first coil. In these arrangements, the second coils and third coils may be disposed in alternating arrangement with one another around the circumference of the lumen. All of the second coils may be electrically connected in series with one another, whereas all of the third coils may be connected in series with one another.

In yet another preferred arrangement, the second transducer assembly includes coils with saddle-shaped turns. Each such saddle-shaped turn may include a pair of spaced-apart runs extending in the first or lengthwise direction and a pair of arcuate runs partially encircling the lumen. The lengthwise runs of each saddle coil preferably extend parallel to and adjacent the lengthwise runs of the other saddle coil, whereas the arcuate runs of the saddle coils extend around opposite sides of the lumen. The third transducer assembly may include a similar pair of saddle coils, and all of the saddle coils may overlap the helical coil of the first transducer assembly. The foregoing arrangements can accommodate the coils or other transducers in a catheter or other small-diameter probe while still leaving adequate room in the probe body for a lumen of reasonable size.

There is also provided in accordance with a preferred embodiment of the invention a method of using a probe having a lumen and a first configuration in which the lumen is obstructed and a second configuration in which the lumen is not obstructed, including:

(a) navigating a probe into a body to a location while the probe is in the first configuration;

(b) changing the configuration of the probe to the second configuration;

(c) performing a medical procedure at the location;

(d) changing the configuration of the probe back to the first configuration; and (e) removing the probe.

Preferably, navigating includes navigating the probe into a body to a location in an intra-body space. Alternatively or additionally, navigating includes navigating the probe using a position sensor mounted on the probe.

BRIEF DESCRIPTION OF THE DRAWINGS

The present invention will be more clearly understood from the following detailed description of the preferred embodiments of the invention and from the attached drawings, in which:

FIG. 6 is a diagrammatic perspective view at a catheter according to a further embodiment of the invention;

FIG. 7 is a diagrammatic sectional view taken along lines 7—7 in FIG. 6;

MODES FOR CARRYING OUT THE INVENTION

Figure 1A:
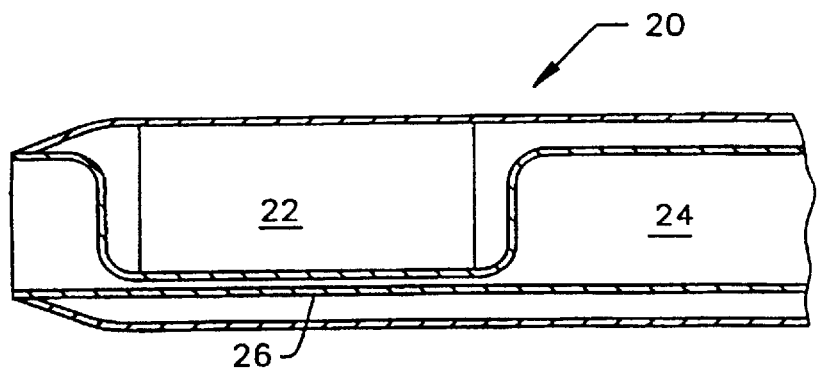
FIG. 1A is a schematic side-view of a catheter, according to a preferred embodiment of the invention, in a compressed configuration.
Figure 1B:
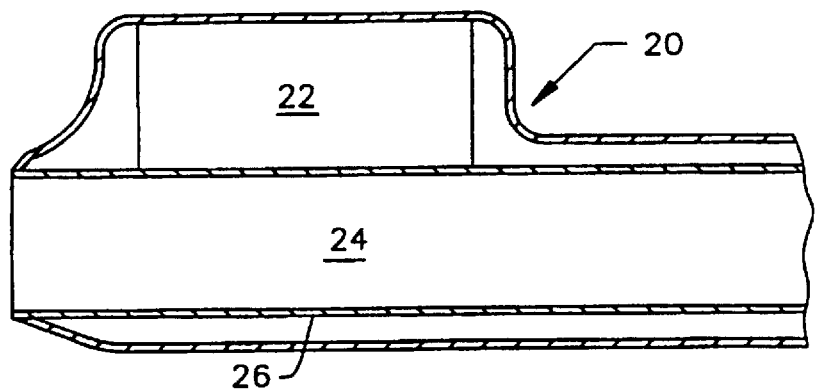
FIG. 1B is a schematic side-view of the catheter of FIG. 1A in an expanded configuration.

FIGS. 1A and 1B show a probe in the form of a catheter 20 having an elongated body 21 defining a lumen 24 extending in the lengthwise or axial direction of the body and lumen. Body 21 is adapted for insertion into the body of a living subject such as a human medical patient or other mammalian subject. Thus, body 21 is formed from materials appropriate for use in the body of the subject, and has a size and shape appropriate for placement in the subject. A position sensor 22 is mounted to body 21 at a sensor location adjacent the distal tip of the probe. As used in this disclosure with reference to an elongated probe for insertion into an object such as a medical probe for insertion into the body of an animal or person, the term "distal" refers to the end of the probe which is inserted into the object first. For example, in a catheter of the type adapted to be threaded into the body through a vein or artery, the distal end of the catheter is the leading end during the threading process. The distal direction is the direction along the length of the probe towards the distal end. The term "proximal" as used herein refers to the end and direction opposite to the distal end and direction.

Catheter 20 which has two configurations: a first, compressed configuration (FIG. 1A) and a second, expanded configuration (FIG. 1B). In the compressed configuration, as shown in FIG. 1A, position sensor 22 compresses a portion 26 of a lumen 24, such that catheter 20 has a substantially constant outside diameter, except for a tapered tip. This geometry is adapted for inserting catheter 20 into the vascular system and conveying it to the heart.

FIG. 1B shows the expanded configuration of catheter 20, in which lumen portion 26 is expanded at the location of sensor 22, so that lumen 24 is substantially straight and has a substantially constant inner diameter thereat. As a result of the expansion of lumen portion 26, position sensor 22 is pushed aside. As a result, catheter 20 bulges near position sensor 22 and has a non-constant outside diameter. However, since the distal end of the catheter is within the heart when the position sensor is pushed aside and the space inside the heart is considerably larger than the catheter, it does not matter that catheter 20 has a larger diameter at its tip. Preferably, catheter 20 is returned to its compressed configuration before removal thereof from the heart to the vascular system. In the first or compressed configuration, the catheter desirably has a diameter at the location of the sensor less than about 5 mm, more preferably less than about 3 mm and most preferably less than about 1 mm.

Preferably, position sensor 22 includes a rotation detector adapted to detect rotation of the catheter tip about the central axis of the catheter. The rotation detector is particularly desirable because, in the expanded state, position sensor 22 is not disposed on the central axis of catheter 20. Thus, the actual position of the catheter will differ from the position of sensor 22; the direction of this difference depends upon the direction from the center of the catheter to sensor 22. This direction is directly correlated with rotation of the catheter tip about its axis. PCT application PCT/US95/01103, the disclosure of which is incorporated herein by reference, discloses a position detection system which incorporates an orientation detector.

Figure 1H:
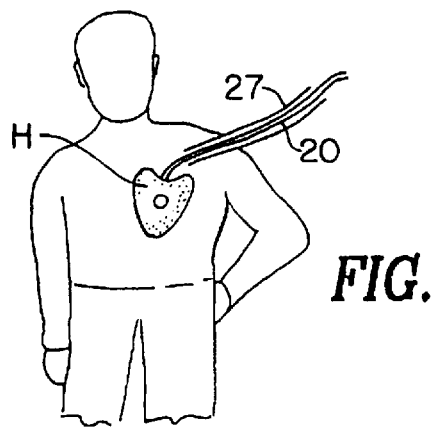
FIG. 1H is a diagrammatic view depicting a catheter according to a further embodiment of the invention in conjunction with a subject.

The casing of catheter 20 is preferably elastic so as to bulge without rupturing when position sensor 22 is pushed aside. One way of changing between compressed and expanded configurations is by guiding catheter 20 into the body in a sheath 27 (FIG. 1H), which starts at the vascular entrance E to the body and ends at the heart H. The sheath is flexible enough so that it can be guided to the heart, however, the sheath does not expand radially, so catheter 20 maintains its compressed configuration while in the sheath. As long as catheter 20 is in the sheath, position sensor 22 is compressed against lumen portion 26. Lumen portion 26 is preferably manufactured from a resilient material. Alternatively or additionally, a so-called "shape memory" or "super-elastic" material which tends to return to a predefined shape when exposed to body temperature. The sheath may move along with the catheter as the catheter is threaded into the heart. Once the catheter tip reaches the heart, the sheath catheter and sheath are moved relative to one another so that the tip or sensor location protrudes from the sheath, whereupon the catheter expands. Thus, once exposed to body temperature, such as in the heart, the catheter expands to the expanded configuration.

Figure 1C:
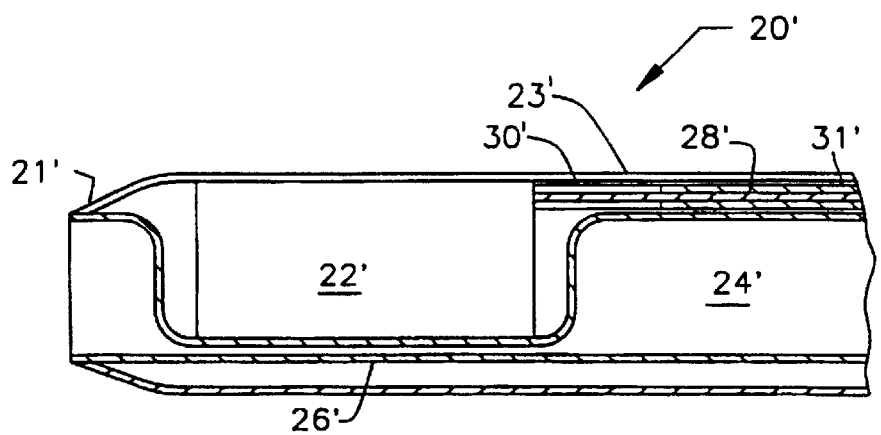
FIG. 1C is a schematic side view of a catheter according to another preferred embodiment of the invention.

FIG. 1C shows another preferred method of changing catheter 20' from a compressed configuration to an expanded configuration. Catheter 20' includes a body 21' having an exterior casing 23' and an interior or first lumen portion 26' defining the first lumen 24', and having a second lumen portion defining a second lumen 31' extending parallel to the first lumen inside casing 23'. The second lumen portion desirably includes a rigid, distal portion 30', which is connected to position sensor 22'. A stylet 28' which is inserted in distal portion 30' urges catheter 20' to a compressed configuration. When stylet 28' is removed from distal portion 30' , catheter 20' can change to the expanded configuration. Preferably, the lumen portion 26' of the catheter body is constructed of a resilient material which urges catheter 20' to its expanded configuration. When stylet 28' is reinserted in distal portion 30', the force that it applies to position sensor 22' is greater than the counter-force exerted by lumen portion 26', so that lumen portion 26' is thereby compressed.

Figure 1D:
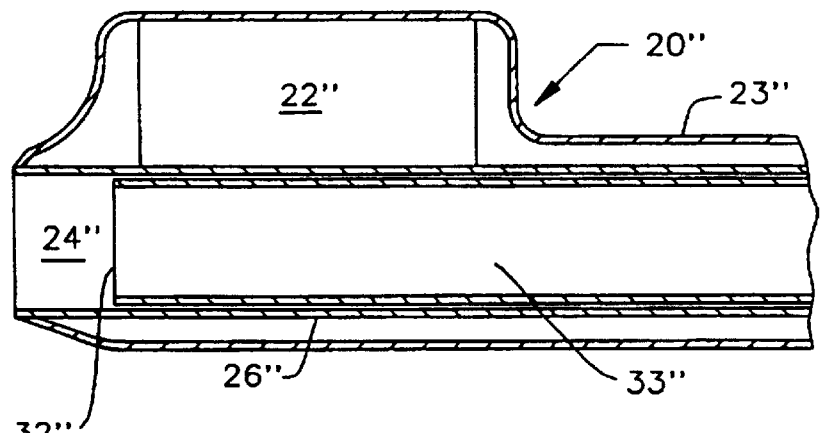
FIG. 1D is a schematic side view of a catheter according to yet another preferred embodiment of the invention.

FIG. 1D shows yet another preferred method of changing catheter 20" from a compressed configuration to an expanded configuration. In this embodiment, catheter 20" is normally in a compressed position. A hollow stylet 32" is inserted into lumen 24" and pushes position sensor 22" aside. Hollow stylet 32" defines a further lumen 33". While the hollow stylet is in place, the environment outside of the catheter at the tip is accessible through the lumen 33" of the stylet. When stylet 32" is withdrawn, the resilience of the exterior casing 23" forces sensor 22" inwardly so that the catheter returns to its compressed configuration.

Figure 1E:
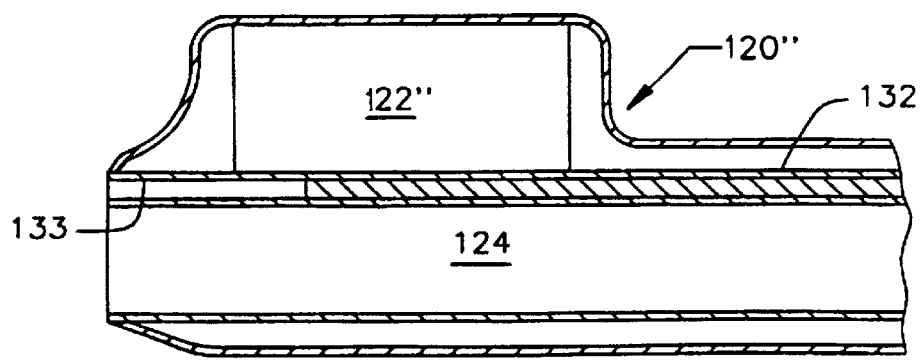
FIG. 1E is a schematic side view of a catheter according to still another preferred embodiment of the invention.

FIG. 1E shows still another preferred method of changing catheter 120 between a compressed configuration and an expanded configuration. In this embodiment, catheter 120 includes a second, small lumen 133 in which stylet 132 is inserted to expand catheter 120.

Figure 1F:
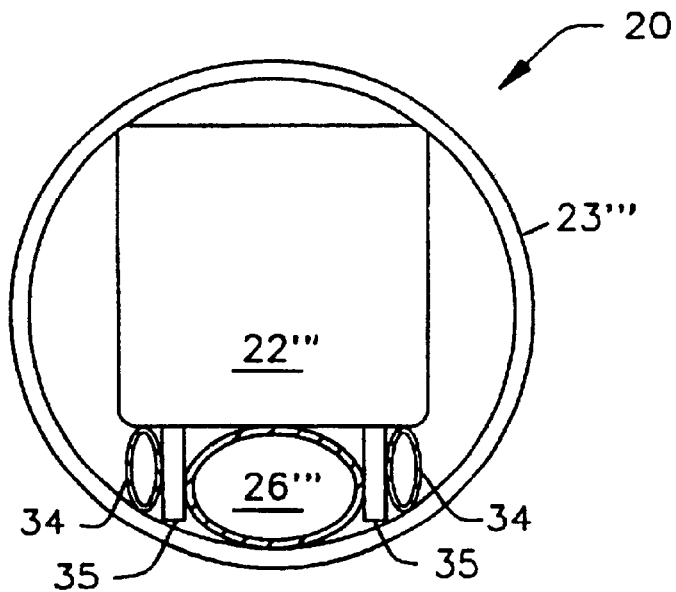
FIG. 1F is a schematic front cross-sectional view of a catheter, according to a preferred embodiment of the invention, in a compressed configuration.
Figure 1G:
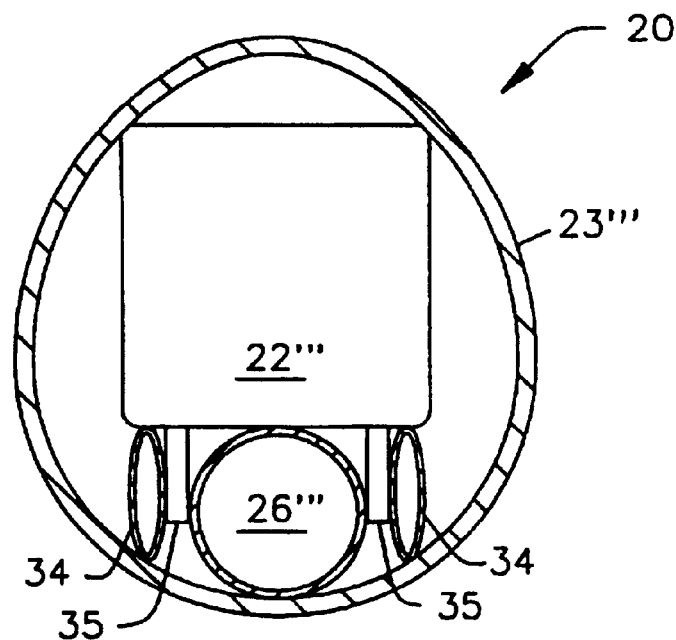
FIG. 1G is a schematic front cross-sectional view of the catheter of FIG. 1F in an expanded configuration.

FIGS. 1F and 1G show still another preferred embodiment of an expandable catheter. In a compressed configuration, shown in FIG. 1F, a plurality of balloons 34 are empty. When changing to an expanded configuration, shown in FIG. 1G, balloons 34 are inflated. As a result, position sensor 22''' is pushed aside and lumen portion 26''' can expand. Balloons 34 are preferably inflated using a liquid, not gas. In order to prevent balloons 34 from compressing portion 26''', balloons 36 are preferably restricted from expanding in the horizontal direction. One preferred type of restriction comprises supports 35 which maintain the horizontal dimension of portion 26'''. Alternatively, the relative forces exerted by portion 26''', the casing 23''' of catheter 20 and balloons 34 are configured so that the combination of the forces exerted by balloons 34 and lumen portion 26''' are enough to overcome the compressive force exerted by the casing 23''' of catheter 20''', while the force exerted by balloons 34 alone is not enough to substantially compress portion 26'''. Preferably, the casing of catheter 20''' is more flexible at the sensor location or tip than at the remainder of the catheter 20'''. Alternatively to balloons 34, other types of expanding mechanisms, may be used.

Figure 2A:
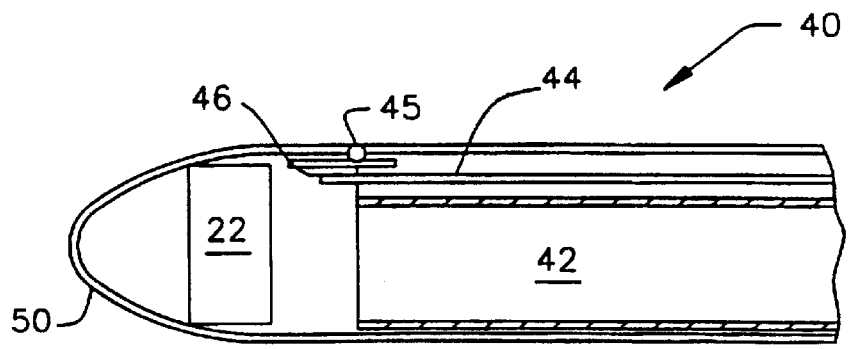
FIGS. 2A and 2B show a catheter having two configurations, one in which its lumen is blocked by a position sensor, and one in which it is not, according to a preferred embodiment of the invention.
Figure 2B:
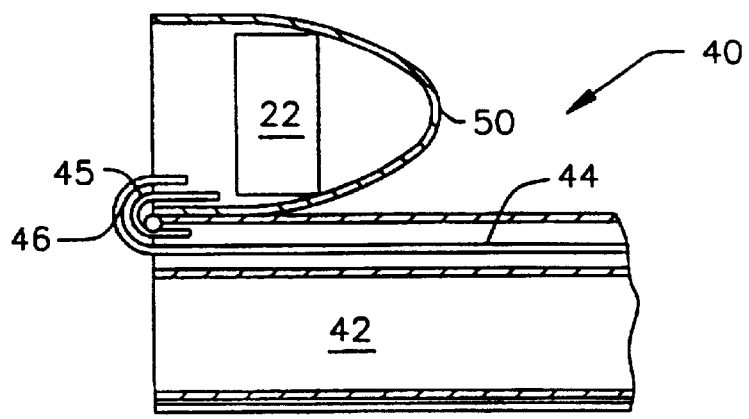

FIGS. 2A and 2B show a catheter 40 having two configurations, one configuration in which a lumen 42 is obstructed by a tip 50 of catheter 20 (FIG. 2A) and one configuration where lumen 42 is substantially unobstructed by tip 50 (FIG. 2B). Tip 50 is pivotable with respect to catheter 40. For example, tip 50 may be pivotally mounted on spring 45.

Figure 2C:
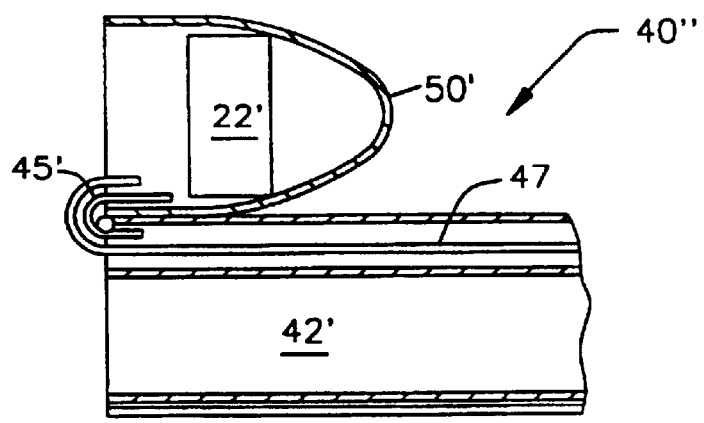
FIG. 2C shows another preferred embodiment of a catheter in which a lumen may be selectively blocked by a position sensor.

In the obstructed configuration, shown in FIG. 2A, lumen 42 extends up to tip 50 and is blocked thereby. In the unobstructed configuration, shown in FIG. 2B, tip 50 is urged aside to a known position, preferably to a folded back position, so that lumen 42 is completely unobstructed. In the non-obstructing position, tip 50 preferably fits into a socket, for example, an indentation formed in catheter 40. Thus, catheter 40 may have an elongated, generally U-shaped indentation extending longitudinally in the vicinity of tip 50, so that tip 50 rests in the groove when in the folded back position. One method of changing from the obstructed state to the unobstructed state is by inserting a curved stylet 44 into catheter 40. The tip of stylet 44 engages a groove 46 in tip 50 and folds tip 50 back over catheter 20. When stylet 44 is removed, tip 50 is urged back to its obstructing position, for example, by a spring 45. FIG. 2C shows an alternative embodiment of catheter 40', in which spring 45' tends to urge tip 50' to its folded back position and tensing means, such as a cable 47, normally keep tip 50' in an obstructing position, closing lumen 42'. Here again, tip 50' carries position sensor 22'

Figure 2D:
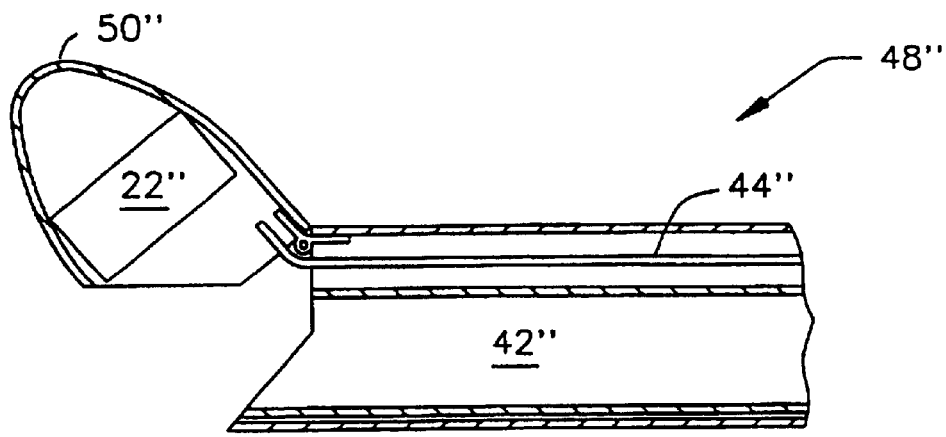
FIG. 2D shows still another preferred embodiment of a catheter in which a lumen may be selectively blocked by a position sensor.

FIG. 2D shows an alternative embodiment of a selectively obstructing catheter 48'', in which tip 50'' is selectively obstructing lumen 42''. Tip 50'' is configured so that it does not substantially obstruct lumen 42'' when it is moved to a relatively small off-axis angle. Thus, the geometry of catheter 48''0 does not change as much as the geometry of catheter 40 (FIGS. 2A and 2B) when changing between obstructing and non-obstructing states.

Figure 3:
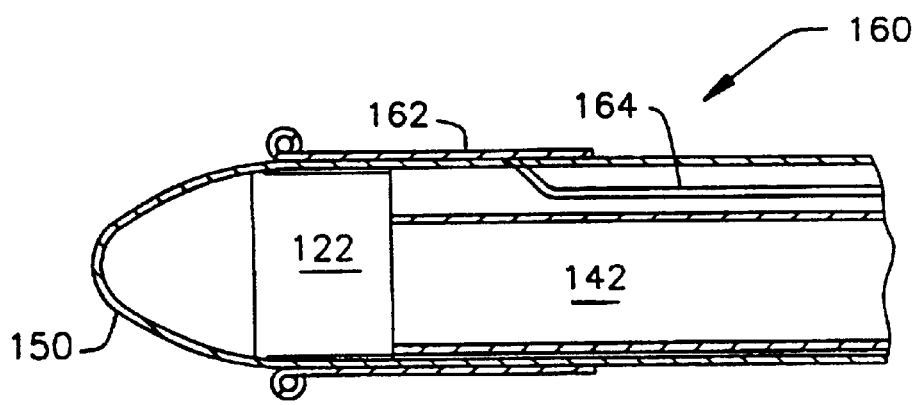
FIG. 3 show a catheter having an external rigid sheath, in accordance with another preferred embodiment of the invention.

FIG. 3 shows an alternative preferred embodiment of a selectively obstructing catheter 160. Catheter 160 has a substantially rigid sheath 162 which keeps tip 150 in a position which blocks lumen 142. Rigid sheath 162 may be relatively short and cover only a proximal portion of tip 150 and a distal portion of catheter 160. Alternatively, sheath 162 may extend along catheter 160 at least until the point where catheter 160 exits the body. Catheter 160 includes apparatus which can move sheath 162 relative to tip 150. Preferably, the moving apparatus includes one or more cables 164, coupled to sheath 162. Where cable 164 moves the sheath in one direction, an elastic element (not shown) may be provided for moving sheath 162 in the opposite direction. In the embodiment where sheath 162 extends outside the body, the body of catheter 160 is preferably moved relative to sheath 162, such as by advancing the body of catheter 160 into sheath 162.

In operation, when sheath 162 is moved away from tip 150, tip 150 moves to a position in which it does not obstruct lumen 142, for example as shown in FIGS. 2B, 2C and 2D. When sheath 162 is moved towards tip 150, the leading edge of sheath 162 urges tip 150 back to its obstructing position. As can be appreciated, sheath 162 can also be used in conjunction with the expanding lumen catheters, described above with reference to FIG. 1A–1H.

In an another embodiment of the invention, a position sensor is mounted on a tool adapted to be inserted in a lumen of a catheter. In operation, the position sensor is inserted into the lumen so that the catheter can be guided to a certain location. Then, the external catheter is fixed at the location, the position sensor tool is removed and other tools, as necessary, are inserted in the lumen.

Figure 4A:
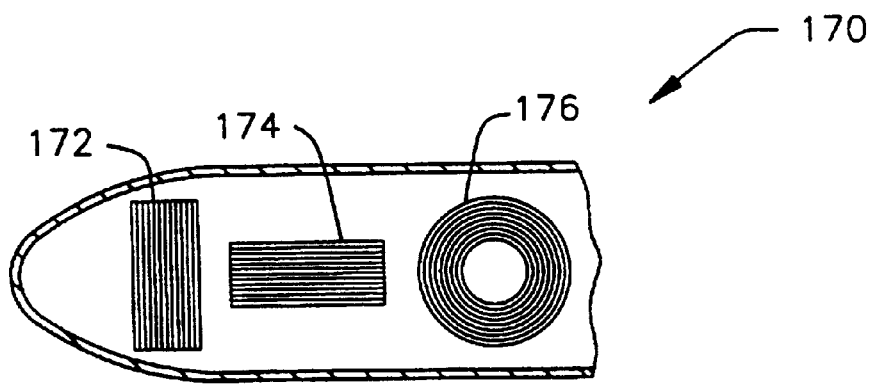
FIG. 4A is a schematic side view of a three coil position sensor.

FIG. 4A shows a catheter 170 with a three coil position sensor, such as disclosed in PCT application PCT/US95/01103. The position sensor comprises three substantially orthogonal coils 172, 174 and 176. Determining the position of catheter 170 may be performed by irradiating the coils with an AC magnetic field generated by a plurality of coils, each of which irradiates at a different frequency or time. The amplitude of the voltages induced in each coil by orthogonal components of the magnetic field are measured so that the location in the field can be determined. Thus, the assembly of coils detects position and orientation by determining characteristics of one or more non-ionizing fields. One problem with the configuration of catheter 170 is that in an catheter having outside diameter less than about 5 mm, and more typically less than about 3 mm, coils 174 and 176 substantially block the entire cross-section of catheter 170, so no lumen is possible.

Figure 4B:
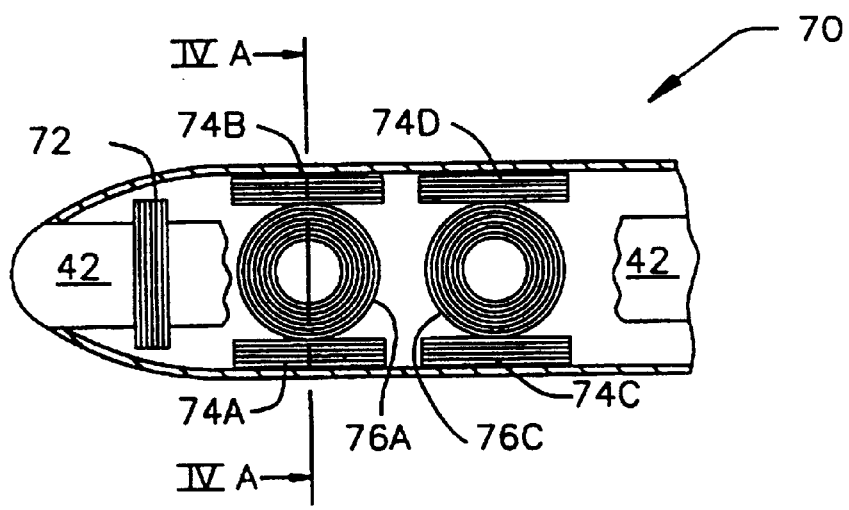
FIG. 4B is a schematic side cross-section of a catheter with a coil based position sensor and a lumen, according to a preferred embodiment of the invention.
Figure 4C:
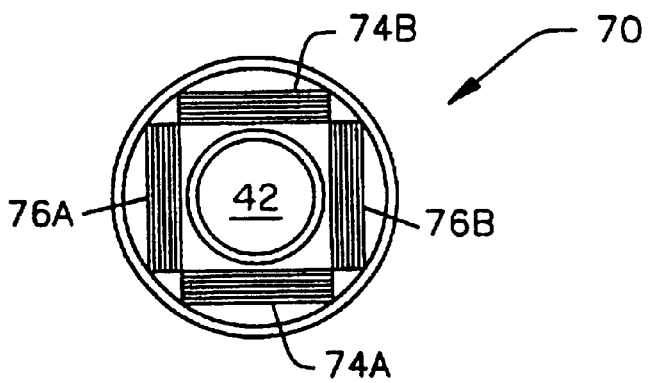
FIG. 4C is a cross-sectional view along line IVA—IVA in FIG. 4B.

FIG. 4B shows a catheter 70 having a three-coil position sensor and a lumen 42. A first coil 72, which corresponds to coil 172 (FIG. 4A), is coaxial with catheter 70, so that it does not substantially obstruct lumen 42. Coil 174 and coil 176, which would have obstructed lumen 42 are each divided into several interconnected coils, none of which obstruct lumen 42. For example, as shown in FIG. 4B, coil 174 is divided into four coils, 74A, 74B, 74C and 74D, which have the same orientation as coil 174. Preferably, coils 74A–D are electrically connected in series. Coil 76 is likewise divided into coils 76A, 76B, 76C and 76D. FIG. 4C is a cross-sectional view of catheter 70 in which coils 74A, 74B, 76A and 76B are shown to flank lumen 42. That is, coils 74A and 74B are offset from one another in a lateral direction, transverse to the lengthwise or axial direction of the catheter and lumen, and coils 74A and 74B are disposed on opposite sides of the lumen from one another. Also, coils 74A and 74B are offset from one coils 74C and 74D in the axial or lengthwise direction.

The length of the position sensor of FIG. 4B is substantially the same as the length of the position sensor of FIG. 4A, however the sensitivity of the position sensor of FIG. 4B may vary from the sensitivity of the sensor of FIG. 4A, depending on the number of windings in each of coils 74A–D and 76A–D and the cross-section of coils 74A–D an 76A–D. Where the size and spacing of the coils permits, a separate ferrite core is provided in each of coils 74A–D and 76A–D. Preferably, the core is ellipsoid so that it does not affect the magnetic field direction in the coil and so that it has a minimal effect on the other coils in the position sensor.

Figure 5A:
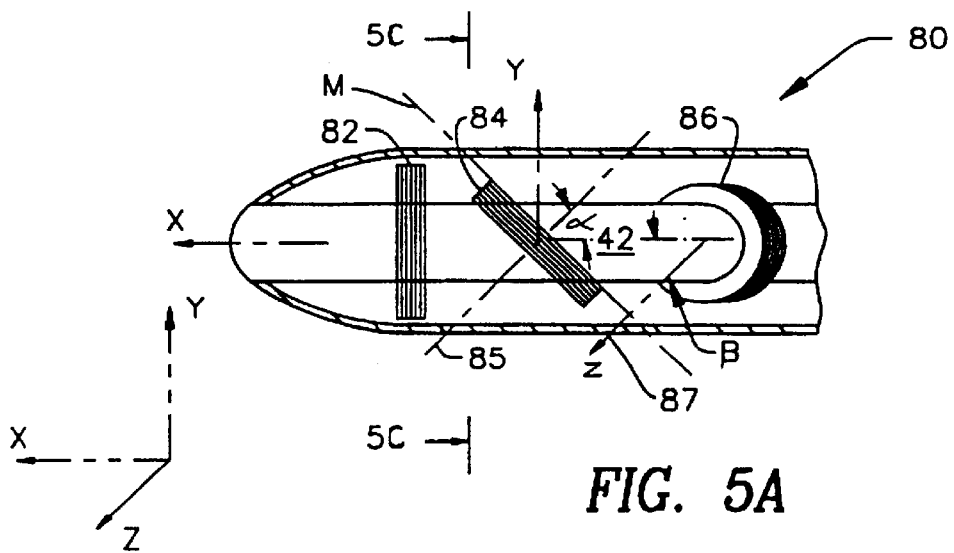
FIG. 5A is a schematic side view of a catheter having coil position sensor in accordance with a preferred embodiment of the invention.
Figure 5C:
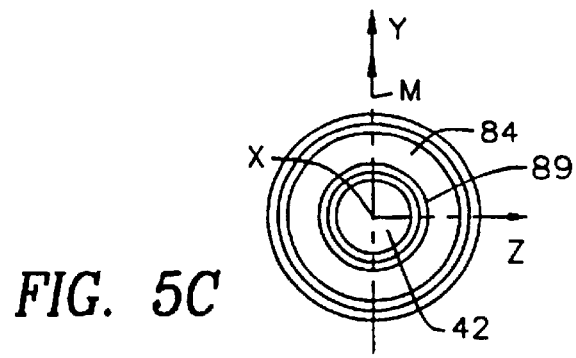
FIG. 5C is a diagrammatic sectional view taken along line 5C—5C in FIG. 5A.

FIG. 5A shows a catheter 80 with a coil-based position sensor according to another embodiment of the invention. Instead of three orthonormal coils, three coils which are not orthonormal are used. However, the orientations of the coils are such that a linear combination of their outputs can give the values of the three orthogonal components of the field. The position detection algorithm is modified to take into account the orientation of coils 82, 84 and 86. Thus, an axial sensing coil 82 has an axis generally parallel to the axis of catheter 80 and turns lying in planes perpendicular to the axis of the catheter. The axial direction is denoted by direction X in FIG. 5. A first lateral sensing coil 84 has an axis 85 which has a component parallel to the axis of catheter 80 and a component which is perpendicular to the axis of the catheter and extends in a first lateral direction Y. The windings of coil 84 lie in planes perpendicular to axis 85. The sensor further includes a second lateral sensing coil 86 having an axis 87 having a component in the X or axial direction and also having a component in a second lateral direction Z, perpendicular to the axial direction X and perpendicular to the first lateral direction Y. In general, the extent of lumen 42 is dependent on the width of coils 84 and 86 and on the angles α and β between coil axes 85 and 87 and the axis of catheter 80. If these angles are too small, so that the winding planes of coils 84 and 86 are almost parallel to one another and almost perpendicular to the axis of the catheter, the amplitude of voltages induced by laterally-directed components of the magnetic field, perpendicular to the axis of catheter 80, is reduced. Where angles α and β are too small, the amplitudes of these voltages may be below the noise level of the system. However, smaller angles α and β and greater parallelism of coils 84 and 86 allow a larger lumen.

In a particular embodiment of the invention, assuming the catheter is parallel to the X axis, α is about 45°, so that the axis of coil 84 is tilted by about 45° to the X axis and about 45° to the Y axis. β may also be about 45°, so the axis of coil 86 is tilted by about 45° to the X axis and about 45° to the Z axis. Alternatively, the angles α and β may be larger, such as up to about 60° or 70° or smaller, such as down to about 30° or 20°. Preferably, the windings of coils 84 and 86, as seen in a view taken along the coil axes 85 and 87 respectively, are ellipsoid shape. Each such ellipsoidal shape has a major axis and a minor axis. These major and minor axes are oriented so that the major axis of each such ellipsoid lies in the plane defined by the axial direction X and by the lateral direction associated with such coil. For example, the major axis M of ellipsoidal coil 84 lies in the plane defined by the first lateral direction Y and the axial direction X. Thus, as seen in projection perpendicular to the axial direction X, as in FIG. 5C, the ellipsoidal coil 84 defines a substantially circular opening 89. The major axis of coil 86 lies in the plane defined by the X and Z directions, so that coil 86 also defines a substantially circular opening when seen in projection perpendicular to the axial direction X. This arrangement maximizes the space available for the lumen 42 within the catheter.

Figure 5B:
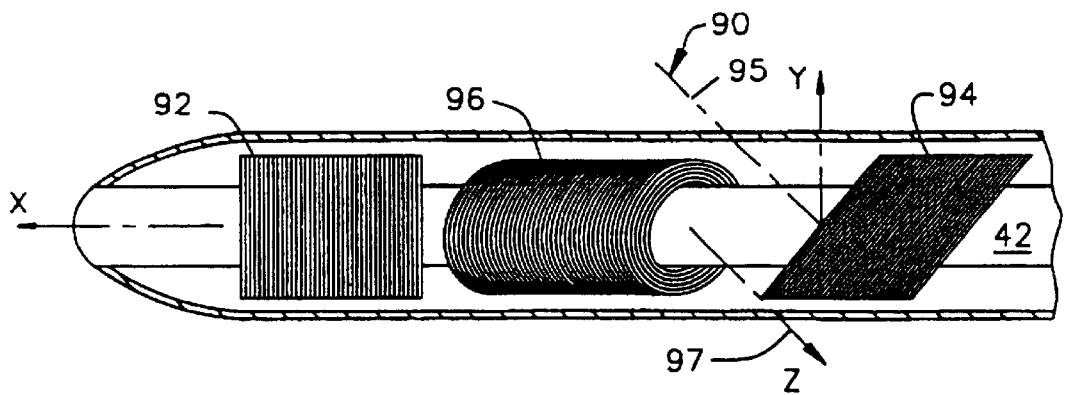
FIG. 5B is a schematic side view of a catheter having coil position sensor in accordance with another preferred embodiment of the invention.

FIG. 5B show a catheter 90 having a coil-based position sensor in accordance with a preferred embodiment of the invention. In this embodiment, the coils have a substantial width. An axial sensing coil 92, having an axis parallel to the X axis, can be similar to coil 172 (FIG. 4A). Lateral sensing coils 94 and a coil 96, which sense field components perpendicular to the X axis, are modified (relative to FIG. 4A) in the following manner. The first lateral sensing coil 94 adapted to sense field components in first lateral direction Y, has a generally cylindrical shape. The axis of this cylinder is parallel to the axial or X axis of the catheter. However, the windings of coil 94 are not perpendicular to the axis of coil 94. Rather, each winding lies in a plane perpendicular to a winding axis 95. Axis 95 has a component in the first lateral direction Y. In effect, each winding of coil 94 is tilted relative to the X axis in the same manner as coil 84 (FIG. 5A) is tilted. direction. Thus, coil 94 can detect field components in the Y direction. Coil 96 has similar windings, but these windings lie in planes perpendicular to winding axes 97, having a component in components in the second lateral direction Z. Preferably, the windings of coils 94 and 96 have an ellipsoidal shape when seen in projection perpendicular to the winding axes. The major axes of the ellipsoidal windings are oriented as described above with reference to the major axes of coils 84 and 86. This arrangement allows lumen 42 a maximal extent and a circular cross-section.

The methods and apparatus for determining field components perpendicular to the catheter axis described with reference to FIGS. 4A–C and 5A–5B may also be applied when a greater or smaller number of coils than three is used.

Although the present invention has been described mainly in the context of a catheter with a position sensor, various embodiment of the present invention, such as those described with reference to FIGS. 1A–G, FIGS. 2A–D and FIG. 3, may be usefully applied even when the device blocking the lumen is not a position sensor, for example, when it is a pressure sensor, a thermal sensor, a pH sensor or other chemical sensor; or a device such as an electrode for sensing electrical potentials in surrounding tissues.

A probe according to a further embodiment of the invention (FIGS. 6 and 7) includes an elongated tubular body 200 such as a catheter tube defining a central bore or lumen 201. The probe includes a sensor 202. Sensor 202 includes a first transducer assembly consisting of a first coil 204. First coil 204 includes a plurality of helical turns encircling lumen 201 and extending around the lengthwise or X direction axis of the body and lumen. The turns of coil 204 thus enclose a projected area in a plane, perpendicular to the X axis. Accordingly, coils 204 are sensitive to changes in magnetic flux directed in the X direction. The center of coil 204 lies at a point 206 within lumen 201.

Sensor 202 further includes a Z direction lateral field transducer assembly including a pair of coils 208a and 208b disposed on opposite sides of lumen 201. Coils 208a and 208b are each generally helical and have turns encircling the turns of coil 204. Coils 208a and 208b have coil axes 210a and coil 210b extending generally in the lateral direction denoted by the Z axis in FIGS. 6 and 7, this lateral direction being orthogonal to the lengthwise or X direction. The turns of coils 208a and 208b encircle the turns of coil 204. Thus, coils 208a and 208b are aligned with the central point 206 of coil 204 in the lengthwise or X direction. Coils 208a and 208b are remote or offset from one another in a further lateral direction denoted by the Y axis in FIGS. 6 and 7, orthogonal to the X and Z directions.

The turns of coils 208a and 208b encircle projected areas in planes perpendicular to the Z direction, i.e., projected areas in planes parallel to the Y and X directions. Coils 208a and 208b thus are sensitive to changes in magnetic flux directed in the Z direction. Coils 208a and 208b are connected in series with one another by an interconnect conductor 212, so that the voltages produced by the two coils are added with one another. The voltage or signal appearing across terminals 214a and 214b thus represents the sum of changes in flux in a first set of projected areas adjacent axis 210a and in a second set of projected areas adjacent axis 210b. The aggregate center of all of these projected areas, taken together is coincident with the central point 206 of coil 204.

The sensor further includes Y direction lateral transducer assembly including a pair or coils 216a and 216b. Coils 216a and 216b have helical turns encircling the turns of coil 204. Coils 216a and 216b extend generally along coil axes 218a and 218b. Coil axes 218 extend in the lateral direction denoted by axis Y in FIGS. 6 and 7, orthogonal to the lengthwise or X direction and also orthogonal to the other lateral direction Z. Thus, each turn of coils 216a and 216b encloses a projected area in the Z-X plane, perpendicular to the Y axis. Here again, the center of area of all such projected areas taken together is coincident with central point 206. Coils 216a and 216b are connected in series by a conductor 220 so that the voltage appearing at terminals 222a and 222b is proportional to the sum of the voltages induced in all of the turns of both coils.

In this arrangement, each transducer assembly measures changes in magnetic flux along a different local direction relative to the sensor, i.e., along the Z, Y, or X axis, but all of the transducer assemblies measure these changes in flux at or adjacent a common central point 206. Thus, provided that the change in flux per unit time in the Z direction is uniform in the Y direction or varies linearly with distance in the Y direction, coils 208 of the Z direction lateral transducer assembly will yield an aggregate voltage equal to the voltage which would be produced by a point transducer located at common point 206. Similarly, provided that the change in flux per unit time in the Y direction is uniform or varies linearly with distance in the Z direction, the Y direction lateral transducer assembly (coils 216a and 216b) will provide a signal equal to that which would be provided by a point sensor at common point 206. The lengthwise or X direction transducer assembly, coil 204, also produces a signal substantially equal to that of a point sensor at common point 206.

The ability to provide signals representing changes in the field components at a common point significantly enhances the accuracy and simplicity of calculations used to deduce the position and orientation of the sensor. Methods for calculating the position and orientation of a sensor are disclosed, for example, in PCT published international application 95/09562 as well as in the aforementioned U.S. Pat. No. 5,480,422 and in U.S. patent application 08/476, 380 the disclosures of which are incorporated by reference herein. These and other calculations are enhanced where the various signals provided by a sensor representing components of the field or changes in components of the field in particular directions all relate to the components or changes in components at the same point. The probes according to this aspect of the invention provide such common point sensitivity while still accommodating a large lumen 201.

Stated more generally, a plurality of transducer assemblies sensitive to field components in different directions will act substantially as point sensors located at a common point and will provide signals representing the components at the common point if the centers of sensitivity of all of the transducer assemblies are located at the same point. As used in this disclosure, the term "center of sensitivity" for any transducer assembly represents the point $\overline{X},\overline{Y},\overline{Z}$, where:

$$\overline{X} = \frac{\int X ds}{\int ds}; \overline{Y} = \frac{\int Y ds}{\int ds}; \text{ and } \overline{Z} = \frac{\int Z ds}{\int ds}; \quad (1)$$

In this formula, X, Y and Z are distances along axes X, Y and Z of space and s is sensitivity of the transducer assembly to the particular component which is to be detected by that transducer assembly. Thus, the incremental value ds represents the sensitivity of an individual incremental portion of the transducer assembly. In each case, the integrals are evaluated over the entirety of the transducer assembly. In the case of a transducer assembly incorporating one or more coils, the center of sensitivity is equal to the aggregate center of the projected areas of the various coils in the transducer assembly. A real device having real components and tolerances normally will not have the centers of sensitivity of all of its transducer assemblies at exactly the same point. However, as used in this disclosure, the centers of sensitivity of the various transducer assemblies may be considered to lie at the same point if the greatest distance between the centers of sensitivity of any two transducer assemblies in the sensor is substantially smaller than the maximum distance between sensitive portions of each single transducer assembly. Preferably, the distances between centers of sensitivity of the various transducer assemblies located in a single sensor are less than about 1.0 mm and preferably less than about 0.5 mm.

The arrangement depicted in FIGS. 6 and 7 provides substantial space for a large lumen 201 in a tubular body 200 of limited diameter. Thus, because the coils 216 and 208 of the two transverse transducer assemblies are disposed in alternating sequence around the circumference of the tubular body and hence around the periphery of lumen 201, these coils can be accommodated within a body 200 of reasonable diameter.

Figure 8:
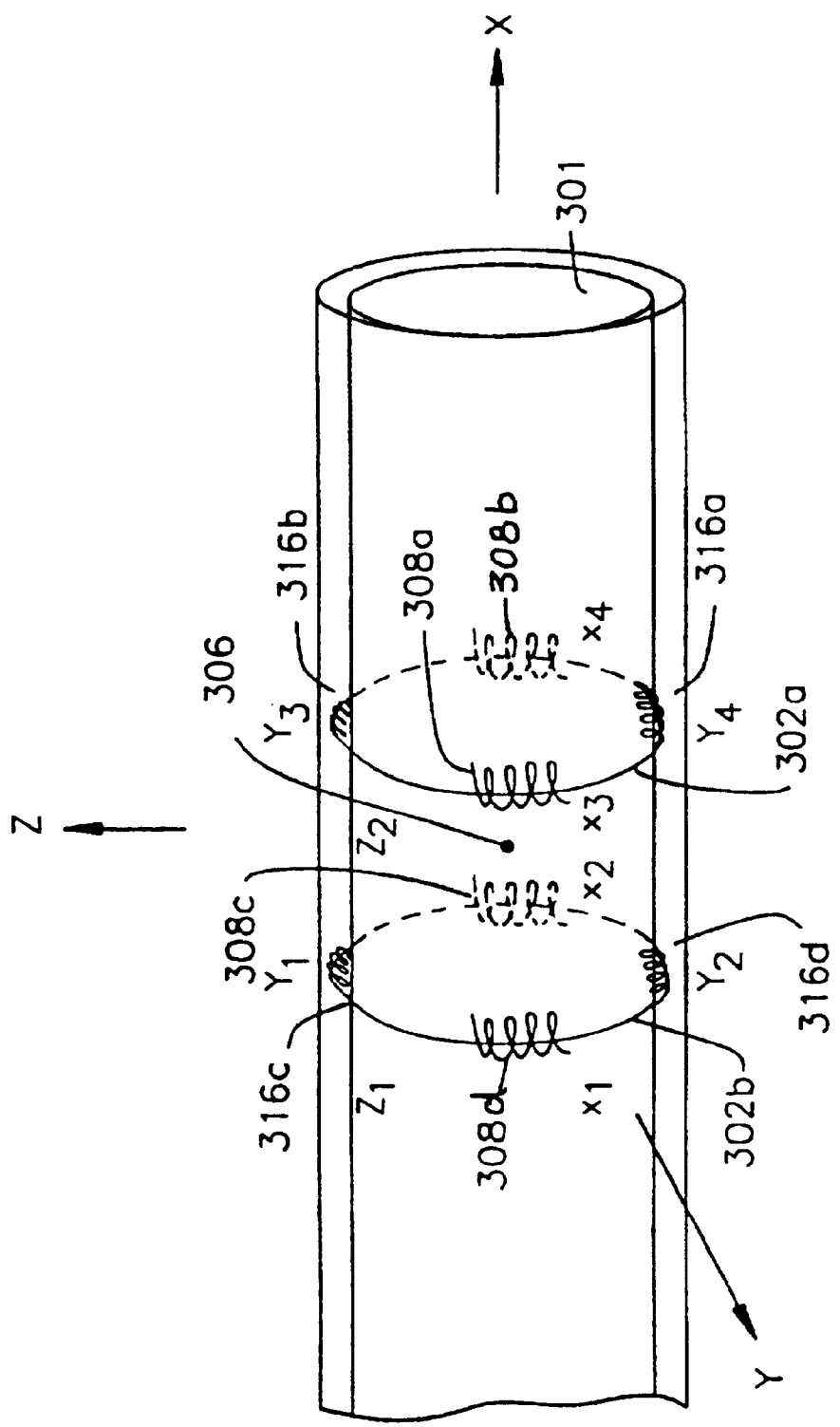
FIGS. 8, 9 and 10 are views similar to FIG. 6, but depicting catheters in accordance with further embodiments of the invention.

In the embodiment of FIG. 8, the lengthwise or X direction transducer assembly includes a helical coil with a pair of separate sections 302a and 302b offset from one another in the lengthwise or X direction. Lateral transducer assembly 308 includes four separate coils 308a–308d. Coils 308a and 308b are disposed on opposite sides of lumen 301 and encircle the windings of a first section 302a of the lengthwise direction transducer assembly, whereas coils 308c and 308d are disclosed on opposite sides of lumen 301 from one another and encircle the windings of the second section 302b of the lengthwise direction transducer assembly.

The other lateral direction transducer assembly includes four coils 316a–316d. Two of these coils 316a and 316b encircle winding 302a whereas the other two coils encircle winding 302b. Here again, all of the coils of each transducer assembly are connected in series so that the signals generated by the coils are added to one another. Once again, the centers of sensitivity of all of the transducer assemblies are located at a common point 306.

Figure 9:
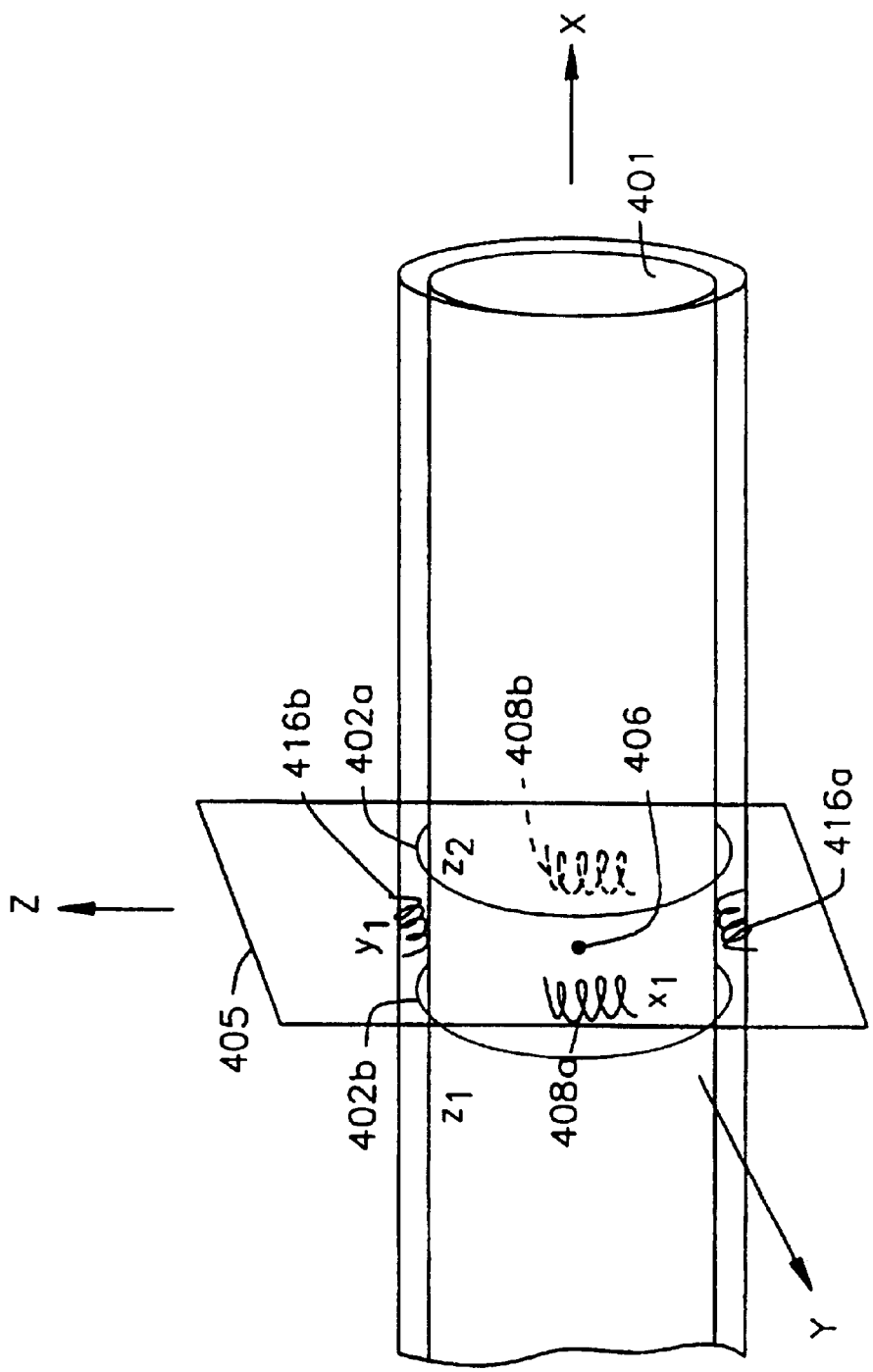

In the arrangement of FIG. 9, the lengthwise transducer assembly also includes a coil having two sections, 402a and 402b. The coils constituting each of the other transducer assemblies are disposed in a common plane 405 positioned axially between sections 402a and 402b. Thus, the coils 416a and 416b of one lateral transducer assembly lie on opposite sides of lumen 401 in this plane, whereas the coils 408a and 408b are oriented transverse to coils 416 but lie in the same plane 405, on opposite sides of lumen 401 from one another. This arrangement also provides all of the transducer assemblies with centers of sensitivity at a common point 406. However, because the coils of the lateral transducer assemblies 408 and 416 are disposed between the sections 402*a* and 402*b* of the lengthwise transducer assembly, there is no need to wind the coils of one transducer assembly around the coils of another. Also, this arrangement can provide a relatively large lumen 401 in a probe body of reasonable diameter. Preferably, the probe is an elongated medical catheter having a diameter or maximum dimension transverse to its axis of elongation, measured at the position sensor, less than about 5 mm, more preferably less than about 3 mm, and most preferably less than about 1 mm. The same features can be used in other medical probes, such as endoscopes, arthroscopes or the like having somewhat longer diameter as, for example, up to about 15 mm, or even larger.

Numerous variations and combinations of the coil arrangements discussed above can be employed. For example, more than two lateral field transducer assemblies can be provided, so as to detect field components in three or more different directions transverse to the lengthwise axis of the probe. In this case, the various lateral directions of sensitivity are non-orthogonal to one another. Further signal processing is required to resolve the various signals into signals representing field components in lateral directions orthogonal to one another. Also, the coils need not be cylindrical helices as pictured, but instead may be polygonal. The coil axes of the coils constituting the lateral transducer assemblies may be curved so that they wrap partially around the circumference of the coil. For example, in the embodiment of FIGS. 6 and 7, the coil axes 210 and 218 may be curved to follow the curvature of coils 204, so that each coil 208 and 216 of the lateral transducer assemblies is in the shape of a section of a torus centered at the common point of the sensor.

Figure 10:
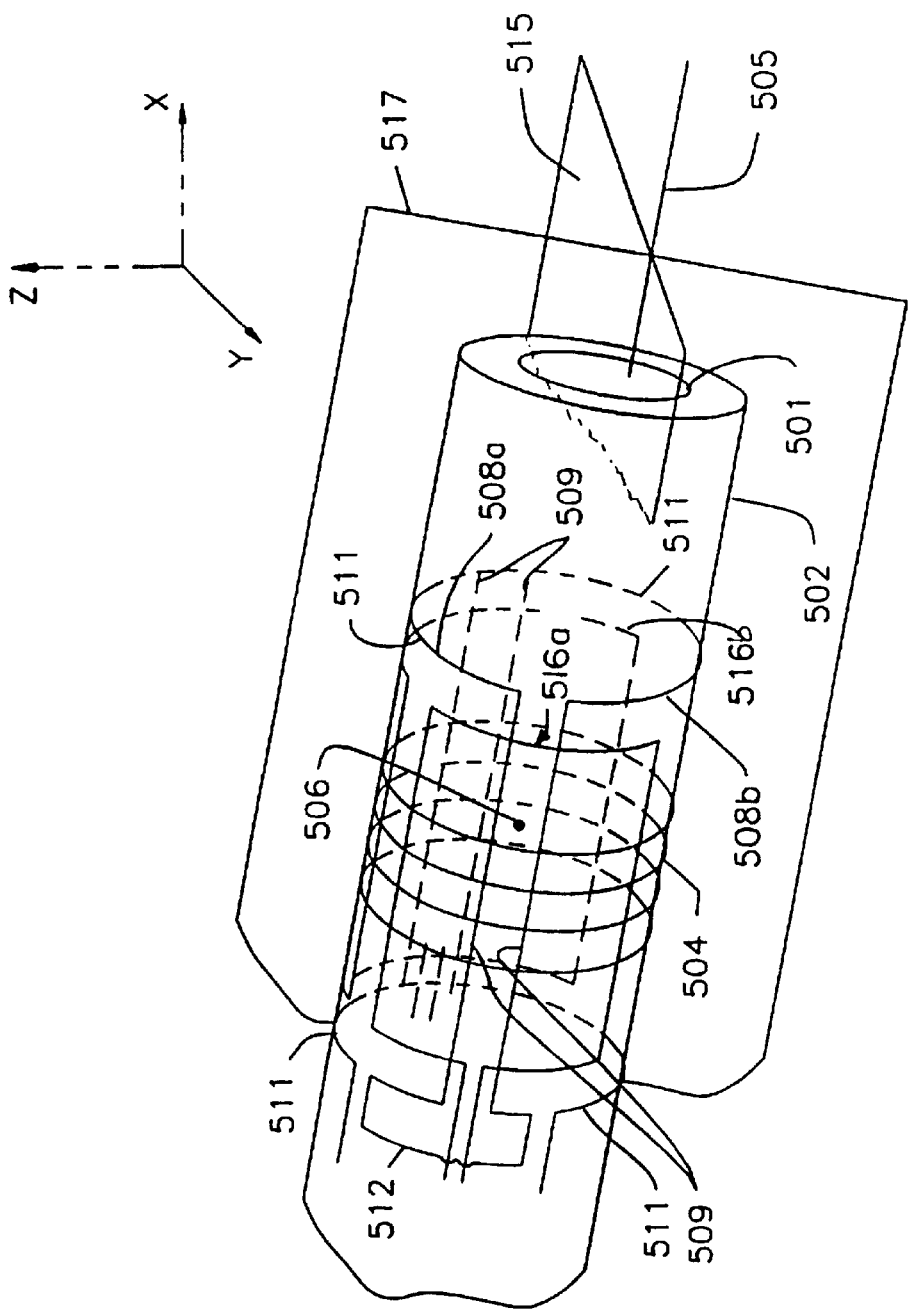

A probe according to a further embodiment of the invention (FIG. 10) incorporates a tubular body 502 and lumen 501 as discussed above, together with a helical coil 504 extending around the circumference of the body and encircling a first or lengthwise axis 505 coincident with the axis of lumen 501. Coil 504 forms a lengthwise transducer assembly. This probe further includes a lateral transducer assembly incorporating a pair of saddle coils 508*a* and 508*b* electrically connected in series. Saddle coil 508*a* includes one or more saddle-shaped turns. For clarity of illustration, only one such turn of each such saddle coil is depicted in FIG. 10. However, in the preferred arrangement each saddle coil may include numerous saddle-shaped turns nested within one another. Each saddle-shaped turn of coil 508*a* includes a pair of lengthwise runs 509 extending in the lengthwise direction along body 502. Each saddle-shaped turn also includes a pair of arcuate runs 511 extending partially around the circumference of body 502 and hence extending partially around lumen 501. Each saddle-shaped turn of the opposite coil 508*b* also includes lengthwise runs 509 and arcuate runs 511. Coils 508*a* and 508*b* are connected in series by a conductor 512. Each turn of coil 508*a*, and each turn of coil 508*b*, encompasses a projected area in a plane 515, orthogonal to the Z axis and parallel to the lengthwise or X axis 505 of the body. The lengthwise runs 509 of coil 508*a* lie on one side of this plane, with the arcuate runs extending away from the plane, whereas the lengthwise runs 509 of the other saddle coil 508*b* lie on the opposite side of plane 515. The arcuate runs of coil 508*b* extend away from plane 515 in the opposite direction from the arcuate runs 511 of coil 508*a*. Thus, the arcuate runs of the two coils extend around opposite sides of the probe body and around opposite sides of lumen 501. The saddle-shaped coils provide relatively large projected areas in plane 515 and hence are sensitive to changes in magnetic flux directed in the lateral action perpendicular to plane 515, i.e., in the lateral direction denoted by the Z axis in FIG. 10. Saddle coils 508*a* and 508*b* of the lateral transducer assembly overlap coil 504 of the lengthwise transducer assembly. Both transducer assemblies have centers of sensitivity at a common point 506.

The sensor of FIG. 10 further includes a Y direction lateral transducer assembly incorporating saddle coils 516*a* and 516*b*. These saddle coils are substantially the same as saddle coils 508*a* and 508*b*. However, these coils are oriented so that the projected areas lie in a plane 517 orthogonal to plane 515. Thus, saddle coils 516 are sensitive to changes in flux directed orthogonally to plane 517, in the direction denoted Y in FIG. 10. Coils 516 overlap the other coils and have their center of sensitivity at the same common point 506.

Figure 11:
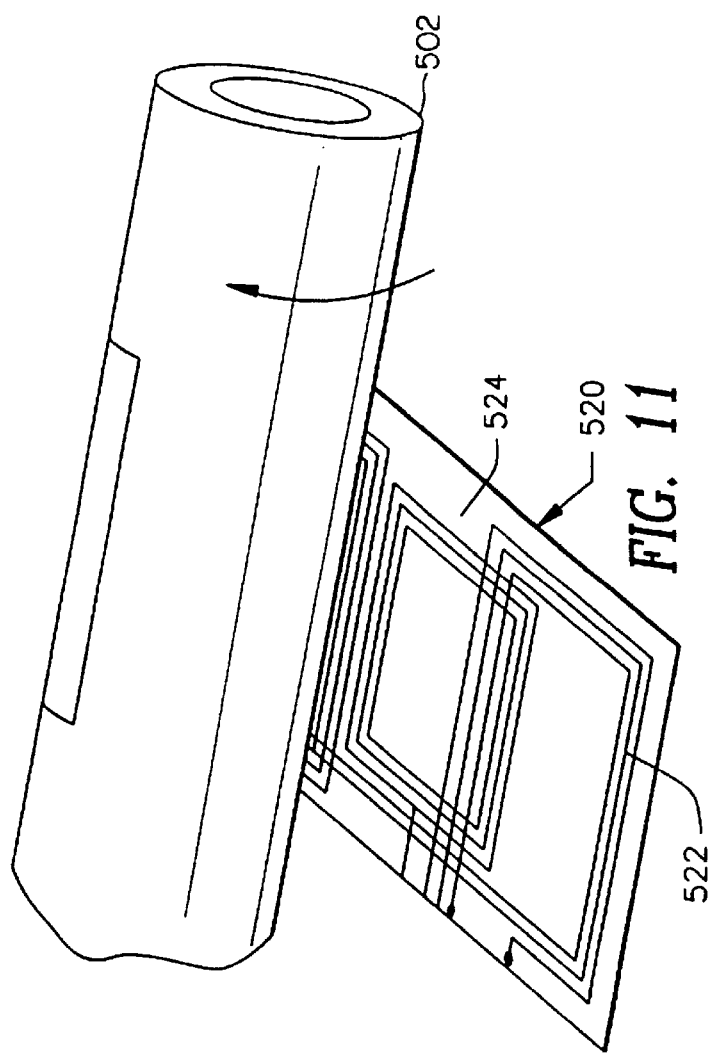
FIG. 11 is a further diagrammatic perspective view depicting any stage in a manufacturing process according to a further embodiment of the invention.

Sensors as shown in FIG. 10 can be fabricated by a process as shown in FIG. 11. In this process, a flexible tape such as a flexible dielectric film 520 having coils 522 and 524 of conductive material thereon is wrapped onto an exterior surface of body 502 by winding the tape around the circumference of the body. Tape 520 may include a dielectric film such as a layer of polyimide commonly utilized for "flex" circuitry in the microelectronics art. Overlapping coils 522 and 524 are formed on opposite sides of the dielectric film so that the crossing coils are electrically insulated from one another. The conductive coils 522 and 524 may be formed from copper or other conductive materials by common processes such as lithographic processes used in making flexible microelectronic circuitry. For example, the polyimide sheet can be provided with continuous layers of copper on opposite sides, and the loops can be formed by masking the layers and etching away unmasked portions. A preferred lithographic coil has a size of 0.8 mm wide by 3 mm long, a thickness of 0.3 mm and includes a rectangular coil having the following characteristics: a line width of 6 $\mu$, a line spacing of 6 $\mu$ and a line thickness of 2 $\mu$. The number of windings is preferably the maximum number which fit in the coil. A thin (0.3 mm) ferrite layer may be provided adjacent the coil to increase its sensitivity. Preferably, more than one layer of conduction lines is provided. The helical coil 504 may be wound around the body before or after application of tape 520. The entire assembly may be covered in a protective outer sheath or coating (not shown).

Figure 12:
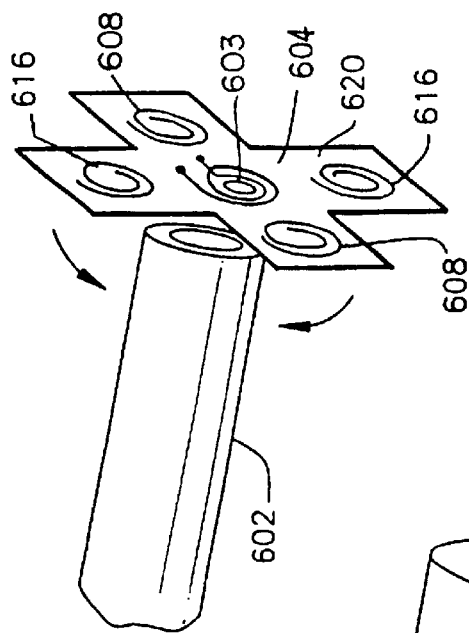
FIG. 12 is a view similar to FIG. 11, but depicting a process according to another embodiment of the invention.

In an alternate process (FIG. 12), the coils may be formed on a flat sheet of a flexible film 620. A hole 603 may be formed in the flexible sheet 620 within one coil 604, so that the probe body 602 may be inserted through the hole and portions of the sheet bearing other coils 608 and 616 may be folded back onto the circumferential surface of the probe body 602.

Numerous variations and combinations of the features described above can be utilized. For example, the saddle-shaped coils depicted in FIG. 10 need not have straight runs. The lengthwise runs and actuate runs of each turn can be formed as portions of a continuously curved run.

Figure 13:
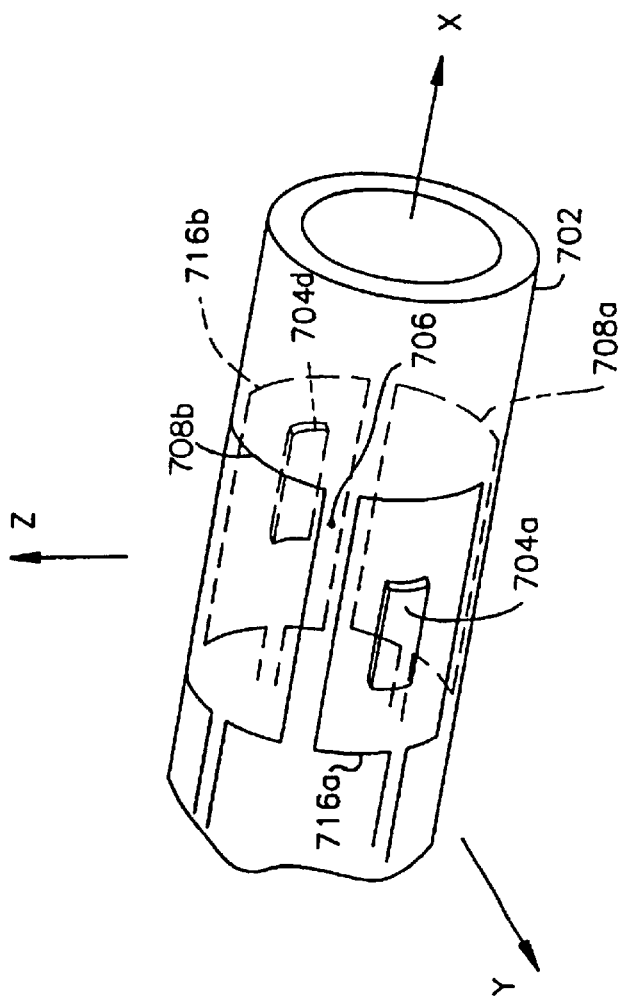

In the arrangements discussed above, all of the transducers are coils. However, the same principles can be applied in fabrication of sensors using transducers other than coils. For example, as shown in FIG. 13, a sensor has lateral transducer assembly 708 sensitive to changes in the field component in a lateral direction Z constituted by a pair of saddle coils 708*a* and 708b as discussed above, whereas the other lateral transducer assembly sensitive to field components in lateral direction Y includes a pair of saddle coils 716a and 716b. The lengthwise transducer assembly sensitive to a field component in the X direction is constituted by a pair of Hall effect or magnetoresistive sensors 704a and 704b mounted to the wall of probe body 702 on opposite sides of lumen 701. Here again, all of the transducer assemblies have their centers of sensitivity at a common point 706.

Figure 14:
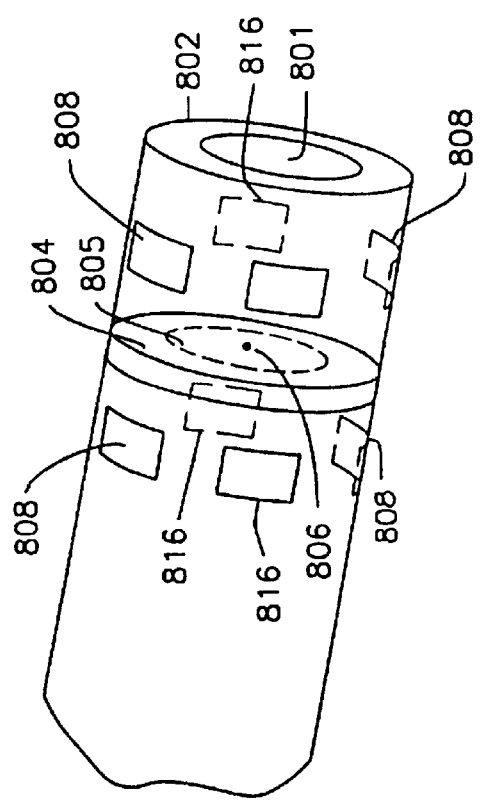
FIGS. 13 and 14 are further views similar to FIG. 6, but depicting additional embodiments of the invention.

In the arrangement of FIG. 14, the axially-sensitive transducer assembly is a flat, washer-shaped solid state magnetic field sensing device such as a magnetoresistive transducer 804 having a hole 805 extending through it in alignment with the bore 801 of the probe body. The other transducer assemblies are constituted by arrays of solid state magnetic field sensing devices such as magnetoresistive elements 808 and 816 disposed around the circumference of the probe body and disposed on opposite sides of axial transducer 804. Here again, the centers of sensitivity of transducer assemblies 804, 808 and 816 all lie at a common point 806. Similar arrangements can be utilized with other forms of transducers including other magnetoresistive transducers (such as those referred to as "giant magnetoresistive" and "colossal magnetoresistive transducers") as well as magnetostrictive transducers, semiconductor transducers such as magnetotransistors, magnetooptical transistors, Hall effect sensors and other forms of transducers capable of detecting magnetic or electromagnetic fields or changes therein.

Figure 15:
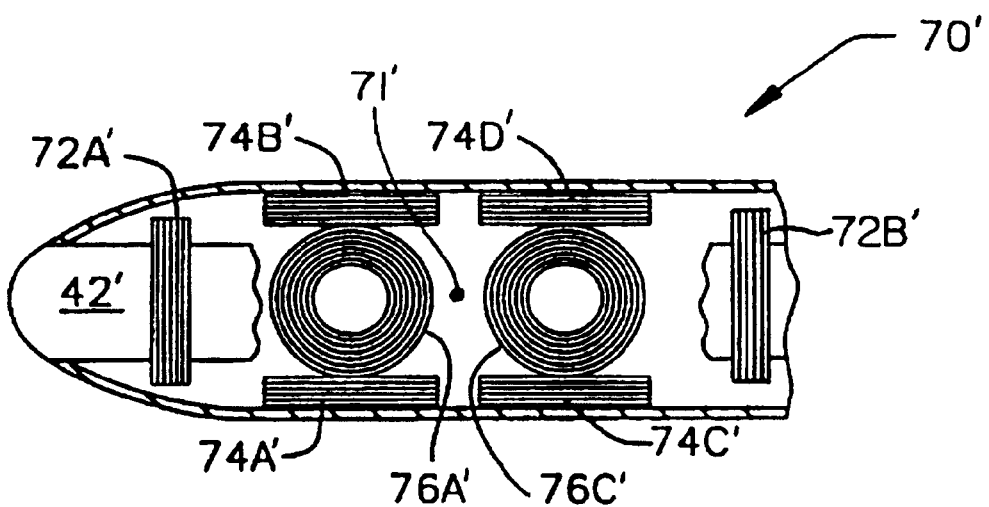
FIG. 15 is a view similar to FIG. 4B but depicting a probe in accordance with a further embodiment of the invention.

As shown in FIG. 15, a probe 70' similar to the probe 70 discussed above with reference to FIGS. 4A and 4B may have its lengthwise or axial-component coil formed as two coil sections 72A' and 72B', so that the center of sensitivity of the lengthwise coil lies at a point 71' between these sections. The arrangement of lateral-component sensing coils is the same as discussed above with reference to FIGS. 4A and 4B. Thus, one such coil includes four sections 74A' through 74D' disposed on opposite sides of the lumen, in two locations along the lumen at equal axial distances from point 71', so that the center of sensitivity of coil 74', considering all of its sections, lies at point 71'. The other coil includes four sections, of which only two sections 76A' and 76C', are visible in FIG. 15. These sections are also arranged at equal distances from point 71', so that the center of sensitivity of coil 76' also lies at point 71'.

The sensitive element of the probes discussed above is referred to herein as a "position sensor" inasmuch as the sensitive element commonly detects a non-ionizing field such as a magnetic, electromagnetic or acoustical field sent from antennas disposed outside of a patient's body during use of the probe and provides signals representing characteristics of the detected field, such that the position and/or orientation of the sensor can be deduced from the sensor signals. Accordingly, the same element can be referred to as a "field transducer." Moreover, the terms "position sensor" and "transducer" as used herein should also be understood as encompassing one or more elements which can send a field for reception by one or more external receiving antennas. For example, any of the coil arrangements discussed above can serve either as a receiving antenna array or as a transmitting antenna array. The terms "position sensor" and "field transducer" should be understood as including transmitting antennas capable of converting signals such as electrical signals into emitted electrical or magnetic fields. These terms should also be understood as referring to elements which can convert electrical signals into light, sonic signals or other non-ionizing fields. For example, certain catheter locating schemes use ultrasonic signals radiated by a transducer in the catheter. As pointed out above, the mounting configurations used herein can also be employed to mount sensors or transducers for other purposes, as, for example, sensors and transducers which detect chemical, electrical, or physical parameters of the body.

It will be appreciated by a person skilled in the art that the present invention is not limited by what has thus far been particularly described. Rather, the present invention is limited only by the claims which follow.

CROSS REFERENCE TO RELATED APPLICATIONS

The present application claims benefit and priority of U.S. Provisional Application No. 60/012,242, filed Feb. 26, 1996, Israeli Patent Application 117,148 filed Feb. 15, 1996, and Israeli Patent Application 119,262 filed Sep. 17, 1996. The disclosures of said applications are hereby incorporated by reference herein.

The following PCT applications, each of which names Biosense, Inc. as an applicant are also incorporated by reference herein:

Catheter Based Surgery filed on or about Feb. 14, 1997 in the Israeli Receiving Office; Intrabody Energy Focusing filed on or about Feb. 14, 1997 in the Israeli Receiving Office; Locatable Biopsy Needle, filed on or about Feb. 14, 1997 in the Israeli Receiving Office; Catheter Calibration and Usage Monitoring filed on or about Feb. 14, 1997 in the Israeli Receiving Office; Precise Position Determination of Endoscopes filed on or about Feb. 14, 1997 in the Israeli Receiving Office; Medical Probes with Field Transducers filed Feb. 14, 1997 in the United States Receiving Office; Medical Procedures and Apparatus Using Intrabody Probes filed Feb. 14, 1997 in the United States Receiving Office; Movable Transmit or Receive Coils for Location System filed Feb. 14, 1997 in the United States Receiving Office; and Independently Positionable Transducers for Location System filed Feb. 14, 1997 in the United States Receiving Office. The PCT application entitled, Multi-Element Energy Focusing, filed Feb. 14, 1996 in the Israeli Receiving Office naming Victor Spivak as applicant is also incorporated by reference herein.

INDUSTRIAL APPLICABILITY

The invention can be used in medical and related procedures.

What is claimed is:

1. A medical probe comprising:
   (a) a probe body adapted for insertion into a living subject, said probe body defining a lumen therein; and
   (b) a blocking portion within the probe body comprising a sensor which obstructs the lumen in a first configuration of the probe and does not obstruct the lumen in a second configuration of the probe.

2. A probe as claimed in claim 1, wherein said sensor includes a position detector.

3. A probe according to claim 2, wherein the position detector comprises a sensor which senses the rotation of the probe.

4. A probe as claimed in claim 3 wherein said body is elongated and defines proximal and distal ends, said lumen extends proximally and distally within said body and wherein said sensor is mounted to said body at a sensor location adjacent said distal end.

5. A probe according to claim 4, wherein, in the first configuration, the probe has a first diameter at said sensor location and wherein, in said second configuration the probe has a second diameter at said sensor location larger than said first diameter.

6. A probe as claimed in claim 5 wherein said first diameter is substantially equal to the diameter of said probe at a location remote from said sensor location.

7. A probe according to claim 1, further comprising an inflatable portion for changing the probe from the first configuration to the second configuration.

8. A probe according to claim 1, further comprising a stylet, which is operative to change the probe between the two configurations.

9. A probe according to claim 8, wherein the stylet is a hollow stylet adapted for insertion into said lumen.

10. A probe according to claim 1, wherein the probe is biased to the second configuration, the probe further comprising a substantially rigid sheath movably mounted to said probe body and surrounding at least a portion of the probe, said sheath being movable between a first position in which said sheath maintains the probe the first configuration and a second position in which said sheath does not maintain said probe in said first position.

11. A medical probe comprising:
  (a) a body adapted for insertion into a living subject, said body having a lumen formed therein; and
  (b) a tip at the distal end of the probe which selectably obstructs the lumen,
  wherein, the probe has a first configuration in which the tip obstructs the lumen, and a second configuration in which the tip is moved aside so that the lumen is substantially unblocked; and wherein the probe is biased to the second configuration, the probe further comprising a substantially rigid sheath movably mounted to said probe body and surrounding at least a portion of the probe, said sheath being movable between a first position in which said sheath maintains the probe the first configuration and a second position in which said sheath does not maintain said probe in said first position.

12. A probe according to claim 11, wherein the tip is moved aside to a known position in the second configuration.

13. A probe according to claim 12, comprising a stylet which engages the tip and moves it from one configuration to the other.

14. A probe according to claim 13, wherein the tip comprises a position sensor.

15. A method of using a probe having a lumen therein and a sensor, comprising the steps of:
  (a) navigating the probe into the body of a living subject to a location while said probe is in a first configuration in which said sensor obstructs said lumen of the probe;
  (b) changing the configuration of the probe to a second configuration in which said sensor does not obstruct said lumen of the probe; and
  (c) performing a medical procedure at the location.

16. A method as claimed in claim 15 further comprising the steps of:
  (d) changing the configuration of the probe from said second configuration back to said first configuration after said step of performing a medical procedure and then; and then
  (e) removing the probe from the body.

17. A method according to claim 15 wherein said navigating step comprises navigating the probe using a position sensor mounted on the probe.

18. A method according to claim 17, wherein said navigating step comprises the step of advancing the probe to a location in an intra-body space.

19. A method according to claim 15, wherein the probe comprises a catheter.

* * * * *